US012620482B2

(12) United States Patent
Schrörs et al.

(10) Patent No.: US 12,620,482 B2
(45) Date of Patent: May 5, 2026

(54) SIGNALING DEVICE FOR MEDICAL DEVICES AND PROCEDURES

(71) Applicant: FRESENIUS MEDICAL CARE DEUTSCHLAND GMBH, Bad Homburg (DE)

(72) Inventors: Alexander Schrörs, Bad Homburg (DE); Annika Thissen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 18/867,809

(22) PCT Filed: May 23, 2023

(86) PCT No.: PCT/EP2023/063714
§ 371 (c)(1),
(2) Date: Nov. 21, 2024

(87) PCT Pub. No.: WO2023/227565
PCT Pub. Date: Nov. 30, 2023

(65) Prior Publication Data
US 2025/0259742 A1 Aug. 14, 2025

(30) Foreign Application Priority Data

May 23, 2022 (LU) .................................. LU502137

(51) Int. Cl.
*G16H 40/40* (2018.01)
*G08B 3/10* (2006.01)
*G16H 10/60* (2018.01)

(52) U.S. Cl.
CPC ............... *G16H 40/40* (2018.01); *G08B 3/10* (2013.01); *G16H 10/60* (2018.01)

(58) Field of Classification Search
CPC ........ G16H 40/40; G16H 10/60; G16H 40/63; G16H 20/17; G16H 20/40; G08B 3/10
See application file for complete search history.

(56) References Cited

U.S. PATENT DOCUMENTS

2015/0229782 A1* 8/2015 Zuidema ............... H04M 19/04
455/418

FOREIGN PATENT DOCUMENTS

EP 2775463 A1 * 9/2014 ............ G08B 21/22
EP 3926641 A1 12/2021
JP 2009077869 A 4/2009

OTHER PUBLICATIONS

Koomen et al. "Reducing medical device alarms by an order of magnitude: A human factors approach." Anaesth Intensive Care. Jan. 2021; 49(1):52-61.), (Year: 2021).*

(Continued)

*Primary Examiner* — Linh Giang Le
(74) *Attorney, Agent, or Firm* — Kilyk & Bowersox, P.L.L.C.

(57) ABSTRACT

The present invention is situated in the field of messaging apparatuses, in particular for medical technology devices. A messaging apparatus and method are suggested according to which the intensity with which a message is output is dependent on an effort parameter and the distance of a person from the apparatus that outputs the message.

17 Claims, 2 Drawing Sheets

(56)         References Cited

OTHER PUBLICATIONS

International Search Report and Written Opinion (with English translation of International Search Report) issued in corresponding International Patent Application No. PCT/EP2023/063714 mailed Aug. 21, 2023 (11 pages).
Sessa, "Guidelines for medical alarm system software design," Altran Italia, Technology Review #8, Oct. 1, 2012, http://admin. altran.it/fileadmin/medias/IT.altran.it/Images/Publication/ TechnologyReview/Technology_Review_n._8_-_Ottobre_2012_P. Sessa.pdf, pp. 16-27.

* cited by examiner

SIGNALING DEVICE FOR MEDICAL DEVICES AND PROCEDURES

This application is a National Stage Application of PCT/EP2023/063714, filed May 23, 2023, which claims priority to Luxembourg Patent Application No. LU502137, filed May 23, 2022.

TECHNICAL FIELD

The present invention is situated in the field of messaging apparatuses for monitored devices, in particular for medical technology devices and methods for operating messaging apparatuses of such kind.

BACKGROUND

The present invention can be implemented for any monitored device that outputs messages to users of the devices, wherein said messages entail an action in response to the respective message on the apparatus itself or in connection with the operation of the apparatus. The present invention is particularly suitable for use with medical technology devices.

Medical technology devices are typically equipped with a multiplicity of monitoring instruments which monitor the proper operation of the technology device, and in some cases also the treatment that is performed on a patient with the medical technology device. Medical technology devices can also be used to monitor a patient as well as the patient's treatment, or for both purposes. For example, a dialysis machine performs a therapy function on a patient and is often set up to record and monitor machine parameters, treatment parameters and even patient parameters.

If proper operation of said monitoring device is not detected, or if the treatment or patient parameters typically determined by sensors do not fall within predefined limit values, an alarm signal is often output for the purpose of alerting the medical staff, or indeed the patient, to an abnormal condition. This abnormal condition should be remedied as rapidly as possible by intervention on the part of the medical staff or the patient themselves, so that proper operation of the dialysis machine or proper treatment (as prescribed by the physician) of the patient with the dialysis machine is restored.

But it is also often necessary to output messages during proper operation of the medical technology apparatus, which messages are most likely to be noticed by the medical staff or the patient receiving treatment. Messages of such kind may relate for example to the approaching end of a therapy session, necessitating further actions, either on the medical technology device or to the patient receiving treatment with the device. For example, if a dialysis treatment lasting four hours is scheduled on a dialysis machine and the dialysis machine has been sequence-programmed correspondingly, the dialysis machine can issue a message a certain time in advance indicating that the end of treatment is approaching, so that preparations can be made for all the requisite steps for terminating the treatment, thus avoiding any unnecessary delays. In the case of haemodialysis, steps of such kind include for example disconnecting the vascular connections from the patient to the extracorporeal blood circuit of the dialysis treatment, and subsequent wound care at the puncture sites, among others.

Messages or message signals within the meaning of the provisional invention include the aforementioned alarm signals as well as the aforementioned output of other messages.

Messages or message signals of such kind are often audible acoustic signals to inform the responsible staff or the patient reliably without the need for visual contact with the apparatus. But message signals may also be of a visual or haptic nature.

In order to ensure that the message signals can also be received by persons at some distance, the signals are often output with a correspondingly high intensity. This intensity is often felt to be too high when a person is close to the unit.

In many cases, healthcare facilities such as hospitals or doctors' surgeries house many medical technology devices, which are frequently in operation for monitoring and/or treating multiple patients at the same time. Accordingly, many message signals are often output at the same time as well. Consequently, this may result in a situation in which it is no longer possible to reliably distinguish between the individual message signals, and consequently causing the medical staff to become overburdened and confused. The simultaneous output of a large number of message signals may also be perceived as stressful and annoying, particularly when the messages are output as audible acoustic signals.

SUMMARY OF THE INVENTION

The object underlying the present invention is to configure the output of messages for medical technology devices in such a way that the limitations described above are surmounted.

This is achieved according to the invention with a messaging apparatus according to claim 1 and a method according to claim 15.

Given the above, in accordance with claim 1, a messaging apparatus 100 is suggested, comprising a first detection unit 101 for detecting various activation states, an assignment unit 102, in which at least one message and one effort parameter each is associated with the individual activation states, the effort parameter being characteristic of a processing time and/or a typical processing complexity of the activation state, a second detection unit 103 for detecting or determining the distance 401 of at least one person 400 from the apparatus 200, the messaging apparatus 100 being configured in such a way that when a first activation state is detected, the messages associated with the detected first activation state is output with an intensity that depends on a first effort parameter which has been associated with the detected first activation state and on the detected distance of the at least one person 400, or which depends on a second effort parameter, which has been associated with a previously detected second activation state and on the detected distance of the at least one person 400.

A method according to claim 15 is also suggested, that includes the steps detecting 301 various activation states of an apparatus 200, assigning 302 at least one message and one effort parameter each to the individual activation states, the effort parameter being characteristic of a processing time and/or a typical processing complexity of the activation state, detecting or determining 303 the distance 401 of at least one person 400 from the apparatus 200, outputting 304 a message associated with the detected first activation state with an intensity that depends on a first effort parameter which has been associated with the detected first activation state, and on the detected distance of the at least one person 400, or which depends on a second effort parameter, which has been associated with a previously detected second activation state and on the detected distance of the at least one person 400.

The subordinate claims relate to preferred variants.

According to the invention, the first activation state is associated with a current message that is about to be output, and the second activation state is associated with a message that was output previously in time to the current message.

DETAILED DESCRIPTION OF AN EMBODIMENT

Figure 1:
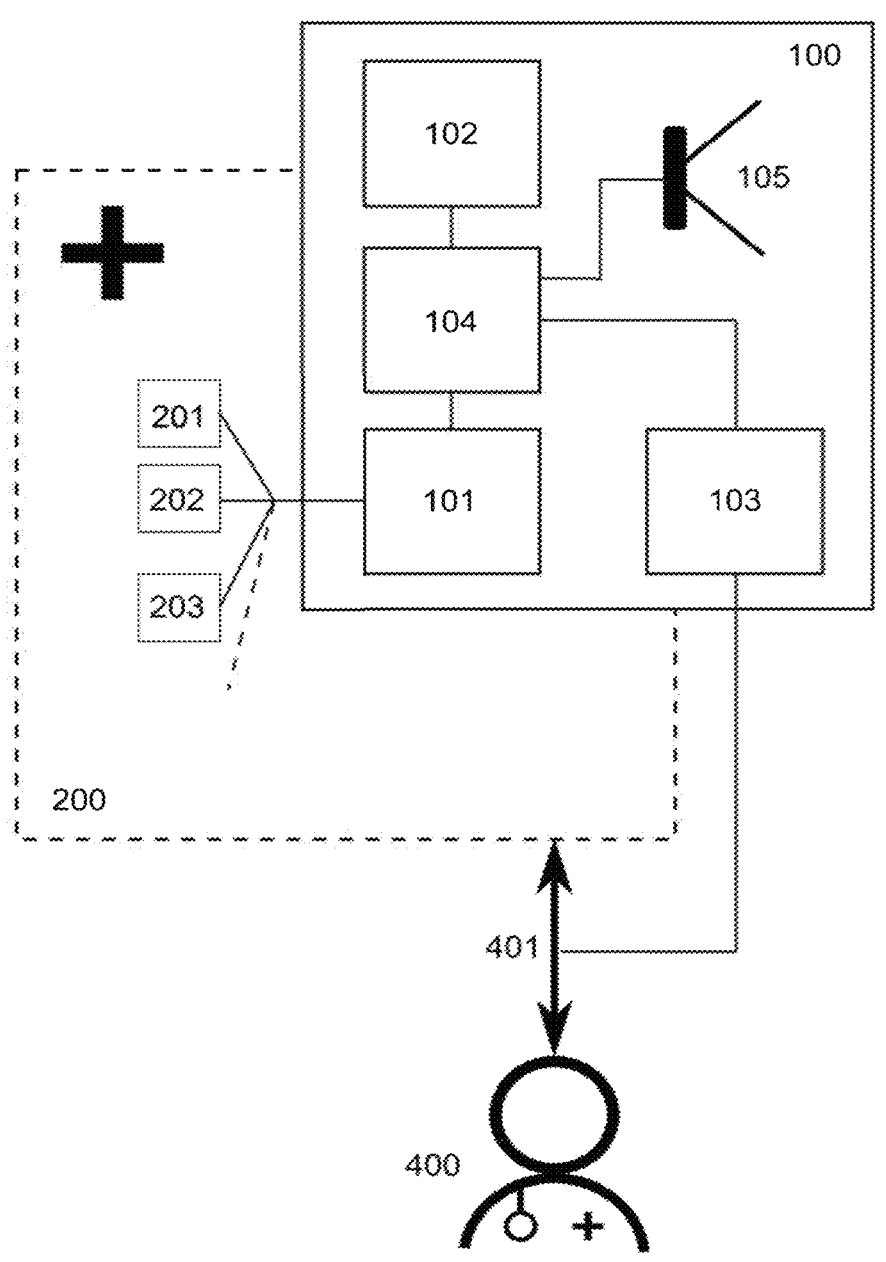
FIG. 1 is a schematic representation of a messaging apparatus according to the invention.

The present invention is based on the understanding that the intensity of a message output by an apparatus to be operated, in particular by a medical technology device, can advantageously be varied depending on the situation in such a way that the load, in particular the acoustic load on the people working with the device is reduced, without any detrimental effect on operational safety. In such a case, the invention exploits the understanding that the output intensity of such a message can advantageously be adjusted such that it depends both on the processing time and/or on a typical processing complexity of actions ensuing from the output message or a previously output message, as well as on the distance between the person to whom the message is addressed and device.

In one aspect of the present invention, a self-learning system is provided in which the above parameters are dynamically adjusted on the basis of system observations.

The invention will be described in the following text with reference to actual exemplary embodiments. In general, all of the apparatuses or apparatus parts described below may be in the form of hardware or software unless otherwise described. Apparatus parts with a specific reference numeral do not have to form a structurally defined unit. The apparatuses or apparatus parts described below are characterized by their function. The actual embodiments of the apparatuses or apparatus parts are of only secondary importance to the invention. Accordingly, different apparatuses and apparatus parts may be represented by the same instance.

FIG. 1 shows a schematic representation of an embodiment of the messaging apparatus 100 according to the invention. The messaging apparatus 100 serves to detect various activation states of an apparatus 200, which is outlined with dashed lines in FIG. 1 and may contain a multiplicity of components 201, 202 and 203. The components 201, 202 and 203 represent any number of any hardware or software components of the apparatus 200. The state of each component 201, 202, 203 can be monitored by the messaging apparatus 100. For this purpose, the messaging apparatus comprises a first detection unit 101. For this purpose, the first detection unit 101 may include various sensors for determining parameters of the components, or it may be configured to read out sensor data from the apparatus 200 that detect the state of the components 201, 202, 203, for example via appropriately configured data interfaces. Sensors according to the invention are understood for example to be sensors for determining physical or chemical variable, or also software or circuits for determining the state of the software that controls the apparatus 200.

Thus, a component 201, 202 or 203 may for example include software that registers operator input by a user of the apparatus 200 and controls at least parts of the apparatus 200 on the basis thereof. The state of a software program is often characterized by certain memory contents of data memory elements accessed by the software. Such software may assume a state depending on operator inputs that results in a certain message from the messaging apparatus in accordance with the programming. According to the invention, such a state is an activation state because it activates the output of a message associated with the state.

A component 201, 202 or 203 may also be a hardware component. For example, an actuator or sensor of the apparatus 200 or another apparatus that interacts with the apparatus 200. In the case of a dialysis machine, a component 201, 202 or 203 may be for example a blood or dialysate pump, a pressure sensor for detecting blood pressures or other fluid or gas pressures, a conductivity sensor, an optical sensor, a tubing set or a dialysis filter. The essential point is that the component is monitored for a specific state that results in a certain message from the messaging apparatus. According to the invention, such a state is also an activation state, since it activates the output of a message associated with the state.

Thus for example the blood pressure of the extracorporal blood circuit in a dialysis machine may be monitored by a sensor. The output signal from this sensor may assume a state that results in a message.

A message within the meaning of the invention may be an acoustic, optical or haptic signal, and in particular an alarm signal which is output with a certain intensity. A message within the meaning of the invention may also be a text message displayed on a screen or an audible test message that is output via a loudspeaker, and which is output with a certain intensity.

The intensity of acoustic signals is understood in particular to refer to their loudness.

The intensity of haptic signals and messages is understood in particular to refer to the amplitude of the associated motion of the actuator that generates the haptic signal, for example the amplitude of a vibration signal.

The intensity of displayed text signals may be understood in particular to refer to a character size, wherein for the purposes of the present invention larger character sizes represent a higher intensity. The text form or text colour as well as the display mode (flashing text, underlined text, backlit text, bold text, luminosity of the characters on screens, etc.) may also be understood as expressions of intensity. Intensity of displayed and spoken text signals may also be understood to be the content thereof. Thus, for example, a particularly high intensity may be conveyed with characteristic words such as "attention" or "urgent" or "important". Characteristic words of such kind are "signal words" within the meaning of the present invention.

The intensity of optical signals is understood in particular to mean their luminosity. Their colour and appearance (flashing frequency, increasing and/or decreasing luminosity) may also serve as a measure of the intensity of optical signals within the meaning of the invention.

The messages assigned to the individual components on the basis of their activation state are each assigned at least one message and one effort parameter in the assignment unit 102, which is characteristic of a processing time and/or of a typical processing complexity of the respective activation state.

In this context, a processing time is understood to be a time that normally has to be spent by a user of the apparatus to carry out a certain action relating to the message, and a typical processing complexity according to the invention is understood to be a parameter that characterizes the effort entailed by the action relating to the message. In this context, the effort parameter may be expressed with numbers or characters that enable a comparison of various times and efforts.

For example, a certain alarm message, which entails a typical processing time of 10 seconds, may be assigned an effort parameter of 2 (or B).

A different alarm message, which requires a longer processing time and/or entails greater effort, may be assigned an effort parameter of 4 (or D), for example.

The effort parameter may for example indicate whether a message that is output by the apparatus only has to be acknowledged by operator input, or if the message requires actions to be taken by the person to whom the message is addressed. For example, a dialysis machine may output a message some time before the end of the therapy session, to the effect that the therapy will be completed soon. This is a message that requires little or no further responsive action on the part of the medical technician to whom the message is addressed at the apparatus itself, because the treatment will continue as planned. After receiving the message, the medical technician may for example check the status of the therapy and the patient and must therefore approach the dialysis machine. The corresponding message may then simply be acknowledged with an operator entry, and the message is cleared.

A message which entails actions on the part of the person to whom the message is addressed, is for example an alarm message or, in the case of the dialysis machine, also the notification that the therapy has ended. In both cases, the user of the apparatus must usually carry out activities at the apparatus. In the case of an alarm, the cause of the alarm must be identified and remedied. For the example of the end of dialysis treatment, the medical technician must complete extensive activities at the dialysis machine and with the patient.

The assignment described above takes place in the assignment unit 102 or is stored therein.

The second detection unit 103 is configured to detect or determine the distance 401 of at least one person 400 from the device 200. Such a detection unit 103 may comprise, for example, a camera that can determine the distance between objects or people using known imaging or video evaluation methods. Other possible known distance sensors from the prior art, such as ultrasonic sensors, light barriers, capacitive or inductive proximity sensors, radar sensors, etc. are also possible.

In one variant of the invention, the second detection unit 103 or the messaging apparatus 100 is configured to indirectly determine the distance of at least a first person 400 from the apparatus 200, wherein a conclusion regarding the presence of a person near or directly at the apparatus 200 is obtained on the basis of the state of the apparatus 200. For example, operator inputs at an operator interface, to a graphical user interface, for example, can be monitored. If an operator input has been detected, the detection unit concludes for a specified time interval that a person is currently in the vicinity of the apparatus. However, a program sequence status that generally requires the presence of a person at the apparatus may also be utilised. This is particularly the case when preparing the apparatus 200 for proper operation thereof. For example, it is likely that a person will be close to the apparatus 200 when the apparatus is being prepared or equipped for its function. With regard to a dialysis machine, for example, this is the case when it is refitted with single-use medical items such as tubing sets or the dialysis filter, and when filling the fluid-carrying tubing parts (blood tubes and dialysate tubes).

Such refitting processes are often accompanied by corresponding displays on a screen. In addition, sensors on the apparatus can also detect the refitting process or the normal operating process. According to the invention, these sensor signals may also serve to detect a person's proximity to or distance from the apparatus 200.

In one variant of the invention, a current first message is output with an intensity that is proportional to the first effort parameter assigned to the current message and proportional to the detected distance of the person 400 from the apparatus 200. This means that the farther the person 400 is from the apparatus and the higher the effort parameter is, the greater the intensity is, and the nearer the person 400 is to the apparatus and the lower the effort parameter is, the lower the intensity is. According to the invention, the absolute intensity of the output message may depend on further parameters. In this way, it is ensured that the intensity of the output messages is not unnecessarily high, and the operator is still able to draw conclusions about the urgency and extent of the activity entailed by an output message based on the perceived differences in intensity.

According to the invention, the distance of at least a first person 400 from the apparatus 200 can also be determined indirectly by evaluating the effort parameter of a previously output message. For example, if a previously issued second message has a low assigned effort parameter, the second detection unit 103 or the messaging apparatus 100 can be configured in such a way that it determines that the person to whom the message is addressed is not in the spatial proximity in front of the apparatus. Typically, messages with low assigned effort parameters are processed quickly by the person 400 to whom they are addressed, and the person then moves away from the apparatus 200 again. Conversely, it is likely that a person will remain in spatial proximity to the apparatus for longer when a message with a high effort parameter is output. Accordingly, it can be concluded that if another first message is output within a certain time that is assigned to the effort parameter of the second issued message (for example the processing time for which the effort parameter is characteristic), the person 400 to whom the message is directed is located in spatial proximity to the apparatus 200. The indirect determination of the distance of the person 400 from the apparatus 200 when a first message is output using the information about the effort parameter of a previously output second message is carried out while taking into account the time difference between output of the first and second messages.

In one embodiment of the invention, a first message is output with a high intensity if a second message that was assigned a low effort parameter was output previously, and it is output with a low intensity if a second message that was assigned a high effort parameter was output previously. In this context, low intensity and high intensity are to be understood relative to each other.

According to the invention, the absolute intensity of the output message may depend on further parameters and settings.

In the case of a dialysis machine as an embodiment of an apparatus 200, a message may be output with a high intensity after a predetermined period of time has elapsed following a purely informational message which the operator only has to confirm, i.e. a message with a low assigned effort parameter, because in this case it is concluded that the operator is no longer in close proximity to the dialysis machine.

On the other hand, a message that is output after a predetermined time has elapsed following a message with a high effort parameter, for example a pressure alarm message in the extracorporeal blood circulation, is output with a low or lower intensity, since it is concluded that the operator is currently still occupied with remedying the alarm message and is in spatial proximity to the dialysis machine. Therefore, the operator should not be irritated or confused by a new high-intensity message.

In a further variant of the invention, the identity of the at least one person 400 is also detected. Messages within the meaning of the invention may be addressed to specific people. Accordingly, the messages from dialysis machines are directed to medical technicians in general and, optionally, to specific individuals. The second detection unit 103 or the apparatus 100 may be configured so that it can determine the identity of the at least one person detected. This may be done, for example, using known person recognition software (face recognition) and a camera as sensor. It is also conceivable for the evaluation to be performed by other personal recognition apparatuses for uniquely identifying the person. Such apparatuses may comprise, for example, graphic symbols (barcode, QR code) and identifiers on clothing worn by the person, or also electromagnetic signals from devices assigned to the person, such as RF-ID tags or Bluetooth signals from mobile phones the person is carrying, and via which in one variant the person can authenticate themselves, for example by entering a PIN or fingerprint. In general, all known technologies for personal identification are available to those skilled in the art.

According to the invention, the distances 401 of several people 200 from the apparatus 200 can also be determined. In this case, the detected identities of the people 200 can be used to control the intensity of the output first message. For example, if two people are detected in spatial proximity to the apparatus 200, but only one person is identified e.g. as medical staff in the manner described above, only the distance 401 of the person identified as medical staff is significant. If for example two people are detected in spatial proximity to the apparatus 200 and both are identified as medical personnel in the manner described above, the distance 401 of a specific detected person 200 may be significant if the message is characterized as intended for this specific detected person 200. In a variant, the distances 401 of the detected persons 200 may also be significant exclusively or alternatively, for example only the closest distance 401 or only the farthest distance 401 from the apparatus 200. A control unit 104, as an exemplary embodiment of a suitable apparatus, has data access to the above-mentioned recorded and stored data. In this case, the controller 104 is configured to actuate a signalling device 105, represented for exemplary purposes as a loudspeaker in FIG. 1, in such a way that when a first activation state detected by the first detection unit 101, the message assigned to the detected first activation state in the assignment unit 102 it output via the signalling device 105 with an intensity that is dependent on the effort parameter assigned to the detected first activation state and on the detected distance of the at least one person 400 from the device 200, or which is dependent on the effort parameter, which is assigned to a previously detected second activation state, and on the detected distance of the at least one person 400 from the device 200.

In one variant, the closer the person 400 to whom the message 400 is addressed is to the apparatus 200, and the lower the effort parameter that is assigned to the message, the lower the intensity is with which the messages are output.

In principle, the dependence of the intensity of an output message on the distance of the person 400 from the apparatus 200 and the effort parameter of the output message or the effort parameter of a previously output message can be defined arbitrarily and depends on the particular circumstances of the operation of the apparatus 200.

The processing times and effort parameters assigned to the individual messages to be output for the respective activation states may be derived empirically from field observations.

For example, in a haemodialysis machine as an exemplary embodiment of the apparatus 200, if an increase in pressure is detected in the arterial blood tube line upstream of the dialysis filter by the first detection unit 101, this represents an alarm condition, which is an activation state within the meaning of the invention. This activation state is assigned a relatively high effort parameter in the assignment unit 102, since such an activation state usually entails extensive activities by the person to whom the output message is addressed, such as stopping the treatment, checking the extracorporeal blood circuit, if necessary replacing the dialysis filter, etc.

On the other hand, if the first detection unit 101 detects an activation state due to a treatment that will end shortly, then a relatively low effort parameter is assigned in the assignment unit 102, since such an activation state does not entail extensive activities by the person to whom the output message is addressed.

In one variant, person-specific effort parameters may be assigned to the individual activation states in the assignment unit. This is designed to address the fact that different people are able to respond more or less effectively to messages within the meaning of the invention based on their experience or their knowledge and skills. Thus, a person A may process a message generated for a given activation state more quickly than a person B with less experience or knowledge. For this purpose, it is essential to record the identity of at least one person 400 detected by the detection unit 103 as well.

In a further variant, the set intensity of the output message is further dependent on the identity of the at least one person 400 detected by the detection unit 103. Thus for example, people with poor hearing can be addressed with louder alarm sounds than people with normal hearing.

In a further variant, the set intensity of the output message is further dependent on a detected ambient noise level. Thus, for example, in a noisy environment, it can be ensured that output messages are not masked by background noise. The noise level can be detected using any acoustic sensors, and these do not have to be part of the messaging apparatus 100 or apparatus 200. The most important consideration is that the information is made available to the messaging apparatus through the ambient noise level, for example via an appropriately designed interface.

In a further variant, the individual effort parameters can be adapted on the basis of recorded actions of individuals. For example, if it is found that certain messages are always processed faster than they are assigned to the associated activation states in the assignment unit 103, then provision can be made to adapt the effort parameters accordingly. This can be done for a specific individual if their performance is above average, or generally without a specific personal reference if a general reassessment of the effort parameter is advisable based on the recorded actions of many persons.

In a further variant, the messaging apparatus 100 is configured to monitor whether an action that is characteristic of the output message is carried out on the apparatus in response to an output message. If this action does not take place or does not take place within a certain period of time, the message is issued repeatedly in the chronological sequence with ever increasing intensity. This is a way to convey a degree of urgency for resolving or processing the reason for the message.

The intensity of an output message can be determined using mathematical calculations taking into account the above-mentioned captured data. However, it may also be stored in a data memory in such a way that a specific intensity is stored for a given combination of the above-mentioned recorded or stored data.

In principle, an intensity controller may also be present to influence the intensity of all output messages, for example a general volume controller for acoustic messages.

Figure 2:
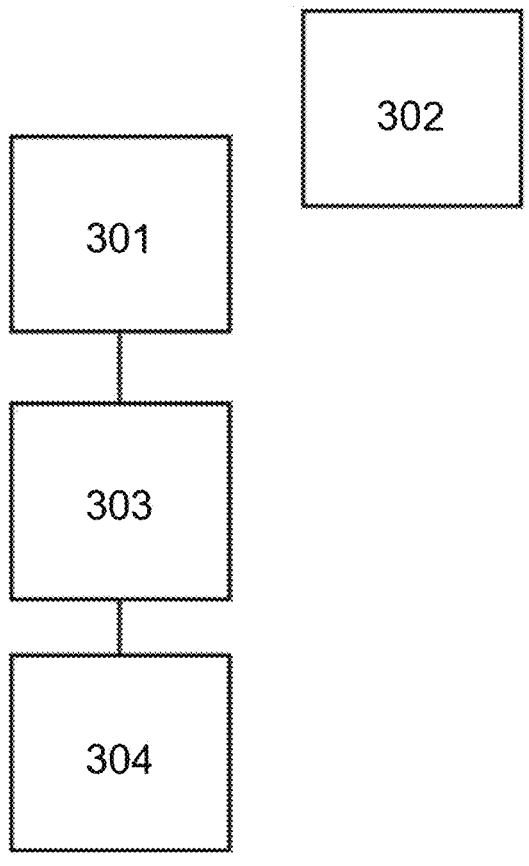
FIG. 2 is a flowchart of a method according to the invention.

FIG. 2 shows a schematic flow diagram of an embodiment of the method according to the invention.

In general, the method may be applied for any apparatus that outputs messages addressed to a user of the apparatus based on detected activation states, or which is configured for this purpose, in particular for medical technology devices. The devices necessary in order to carry out the individual steps in such a situation may include the same devices as described in FIG. 1.

In step 301, an activation state of an apparatus is detected as described in FIG. 1.

Step 302 comprises the assignment of at least one message and at least one effort parameter which is characteristic of a processing time and/or of a typical processing complexity of an activation state to each activation state.

Step 302 typically takes place before the apparatus is operated and usually occurs for multiple activation states. In one variant of the invention, the assignment changes as described above based on observation of the reaction by the user of the device to the output message.

In step 303, the distance 401 or the distance of at least one person 400 from the device 200 is detected or determined. It is irrelevant here by what means or in what way the distance is determined.

In step 304, a message that is assigned to the detected activation state is output with an intensity that is dependent on the effort parameter assigned to the detected activation state and on the detected distance 401 of the at least one person 200, or which is dependent on a second effort parameter, which is assigned to a previously detected second activation state, and on the detected distance of the at least one person 400.

In one variant, the effort parameter and/or the intensity of the output message is further dependent on the identity of the at least one person as described above.

The invention claimed is:

1. A messaging apparatus, comprising
a first detection unit for detecting various activation states of an apparatus,
an assignment unit, in which at least one message and at least one effort parameter that is characteristic for a processing time and/or for a typical processing complexity of the respective activation state is assigned to each of the individual activation states, a second detection unit for detecting or determining the distance of at least one person from the apparatus,
wherein the messaging apparatus is configured such that when a first activation state is detected the message assigned to the detected first activation state is output with an intensity that is dependent on a first effort parameter, which is assigned to the detected first activation state, and on the detected distance of the at least one person, or is dependent on a second effort parameter, which is assigned to a previously detected second activation state, and on the detected distance of the at least one person.

2. The messaging apparatus according to claim 1, wherein the message is an acoustic, optical or haptic signal.

3. The messaging apparatus according to claim 1, wherein the message is a displayed or audibly output text message.

4. The messaging apparatus according to claim 3, wherein the intensity of the output message is varied by signal words in the text message.

5. The messaging apparatus according to claim 1, wherein the intensity of the output message refers to the loudness, the brightness, the appearance, the text form, the text colour or the display mode with which the message is output.

6. The messaging apparatus according to claim 1, comprising an apparatus for determining the personal identity of the at least one person, wherein the intensity of the output message or the at least one effort parameter is additionally influenced by the determined personal identity of the person.

7. The messaging apparatus according to claim 6, wherein the apparatus for determining the personal identity of the at least one person comprises a camera or an apparatus for receiving electromagnetic waves.

8. The messaging apparatus according to claim 1, comprising recording means for recording actions by the at least one person, wherein the at least one effort parameter is dependent on the recorded actions of the at least one person.

9. The messaging apparatus according to claim 1, wherein the intensity of the output message further depends on a detected ambient noise level of the apparatus.

10. The messaging apparatus according to claim 1, wherein the messaging apparatus is configured to monitor whether an action that is characteristic for the output message is performed on the apparatus in response to an output message, and to output the message with a higher intensity in the event that the action is not performed within a predetermined period of time.

11. The messaging apparatus according to claim 1, wherein the second detection unit comprises a camera, an ultrasonic sensor, a light barrier, a capacitive or inductive proximity sensor or a radar sensor.

12. The messaging apparatus according to claim 1, wherein the second detection unit is configured to draw a conclusion from the evaluation of operator inputs into the apparatus as to whether the person is located within operating range in front of the apparatus.

13. The messaging apparatus according to claim 1, wherein the second detection unit is configured to draw a conclusion as to whether the person is located within operating range in front of the apparatus on the basis of the status of a program sequence that controls the apparatus.

14. A medical technology device comprising a messaging apparatus according to claim 1.

15. The medical technology device of claim 14, wherein the medical technology device is a dialysis machine.

16. The messaging apparatus according to claim 1, wherein the message is an alarm signal.

17. A method for outputting a message, comprising the steps:
detecting different activation states of an apparatus,
assigning at least one message and one effort parameter that is characteristic of a processing time and/or of a typical processing complexity of the respective activation state to each of the individual activation states,
detecting or determining a distance of at least one person from the apparatus, outputting a message that is assigned to a detected first activation state, with an intensity that is dependent on a first effort parameter, which is assigned to the detected first activation state, and on the detected distance of the at least one person, or that is dependent on a second effort parameter, which is assigned to a previously detected second activation state and on the detected distance of the at least one person.

\* \* \* \* \*